United States Patent [19]

Marsili et al.

[11] 4,219,478
[45] * Aug. 26, 1980

[54] RIFAMYCIN COMPOUNDS

[75] Inventors: Leonardo Marsili; Vittorio Rossetti; Carmine Pasqualucci, all of Milan, Italy

[73] Assignee: ARCHIFAR Laboratori Chimico Farmacologici S.p.A., Rovereto, Italy

[*] Notice: The portion of the term of this patent subsequent to Apr. 25, 1995, has been disclaimed.

[21] Appl. No.: 913,107

[22] Filed: Jun. 6, 1978

Related U.S. Application Data

[63] Continuation-in-part of Ser. No. 694,589, Jun. 10, 1976, Pat. No. 4,086,225.

[30] Foreign Application Priority Data

Jun. 13, 1975 [IT] Italy .................................. 5174 A/75

[51] Int. Cl.$^2$ ............................................. C07D 491/20
[52] U.S. Cl. ............................... 260/239.3 P; 424/264
[58] Field of Search .................................. 260/239.3 P

[56] References Cited

U.S. PATENT DOCUMENTS 4,086,225   4/1978   Marsili et al. .................. 260/239.3 P

FOREIGN PATENT DOCUMENTS 2626296 12/1976 Fed. Rep. of Germany .... 260/239.3 P

Primary Examiner—Alan L. Rotman
Assistant Examiner—Robert T. Bond
Attorney, Agent, or Firm—Oblon, Fisher, Spivak, McClelland & Maier

[57] ABSTRACT

Oxidized rifamycin compounds having high antibiotic activity as obtained by reacting 3-amino-4-deoxo-4-imino-rifamycin S or related compounds with a ketone.

5 Claims, No Drawings

RIFAMYCIN COMPOUNDS

This application is concerned with an invention related to that disclosed and claimed in our prior application Ser. No. 694,589, filed June 10, 1976, now U.S. Pat. No. 4,086,225, issued Apr. 25, 1978.

The invention of U.S. Pat. No. 4,086,225 and this invention relates to novel rifamycin compounds having high antibiotic activity. Such compounds are selected from the group consisting of the compounds having the following formula:

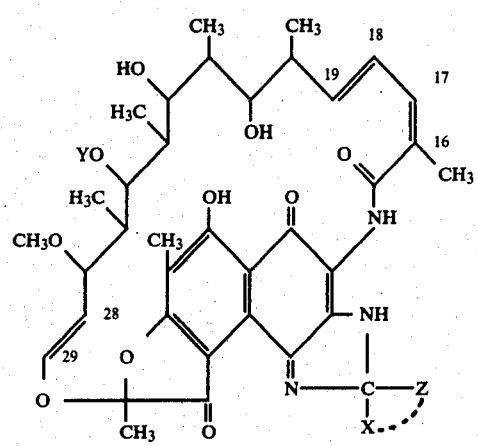

wherein; X is an alkyl having less than 5 carbon atoms; Y is —H or —COCH₃; Z is selected from the group consisting of alkyl with less than 5 carbon atoms, alkoxy-alkyl with less than 6 carbon atoms, hydroxyalkyl with less than 4 carbon atoms, carboxyalkyl with less than 5 carbon atoms, carbalkoxyalkyl with less than 6 carbon atoms, halogen-alkyl with less than 4 carbon atoms, N,N-dialkylaminoalkyl, in particular dialkylaminoalkyl having less than 6 carbon atoms, arylalkyl with less than 10 carbon atoms, cycloalkyl, in particular cycloalkyl having less than 7 carbon atoms, and X and Z along with the C atom to which they are bonded form a ring selected from the group consisting of a hydrocarbon ring with less than 7 carbon atoms, a hydrocarbon ring with less than 7 carbon atoms substituted with at least one radical selected from the group consisting of alkyl with less than 4 carbon atoms, halogen and carbalkoxy, in particular carbalkoxy with less than 4 carbon atoms, a heterocyclic ring with less than 7 atoms containing one N atom, in particular the piperidine ring, a heterocyclic ring with less than 7 atoms, containing one N atom, in particular the piperidine ring, and substituted with a radical selected from the group comprising linear alkyl having from 1 to 8 carbon atoms, branched alkyl having from 3 to 8 carbon atoms, alkenyl having 3 or 4 carbon atoms, cycloalkyl having from 3 to 6 carbon atoms, alkoxyalkyl having from 3 to 7 carbon atoms, arylalkyl with less than 9 carbon atoms, alkyl-furyl having 5 or 6 carbon atoms, alkyl tetrahydrofuryl having 5 or 6 carbon atoms, carbalkoxy, in particular carbalkoxy with less than 4 carbon atoms and alkanoyl having from 2 to 6 carbon atoms, haloalkanoyl having from 2 to 6 carbon atoms and one haloatom only, and 16, 17, 18, 19-tetrahydroderivatives and 16, 17, 18, 19, 28, 29-hexahydroderivates thereof.

The term "aryl" is used herein, to designate aryl hydrocarbon.

In the parent application, Ser. No. 694,589, it is stated that an alkyl substituent on the N-containing heterocyclic ring may have less than 4 carbon atoms and an acyl substituent less than 5 carbon atoms and such substituents are included in the invention common to that of the present invention and that of our Pat. No. 4,086,225, referred to above.

A substituent on the N-containing heterocyclic ring is preferably positioned on a nitrogen atom of that ring.

Rifamycin compounds having antibiotic activity of formula

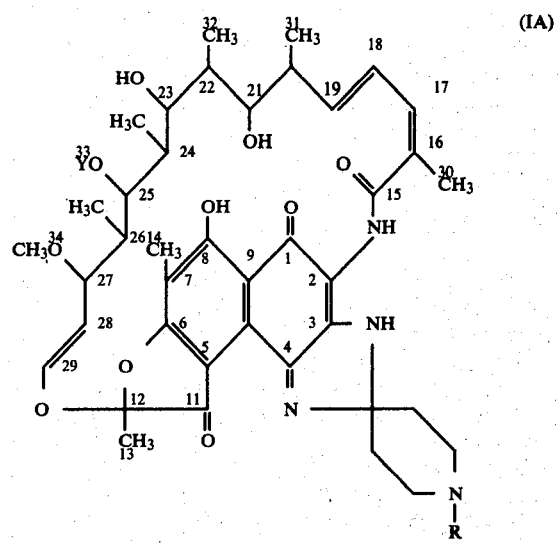

wherein R is a radical selected from the group consisting of linear alkyl having 4 to 8 carbon atoms, branched alkyl having 4 to 8 carbon atoms, alkenyl having 3 or 4 carbon atoms, cycloalkyl having 3 to 6 carbon atoms, alkoxyalkyl having 3 to 7 carbon atoms, alkyl-furyl having 5 or 6 carbon atoms, alkyl tetrahydrofuryl having 5 or 6 carbon atoms, alkanoyl having 5 or 6 carbon atoms, and monohaloalkanoyl having 2 to 6 carbon atoms, and Y is —H or —COCH₃, and their preparation, are the subject of the present invention. Also included in the present invention are 16, 17, 18, 19-tetrahydroderivatives and the 16, 17, 18, 19, 28, 29-hexahydro-derivatives thereof.

Rifamycin compounds according to the present invention have high antibacterial activity, particularly on Mycobacterium Tuberculosis. Such compounds are in the form of powders from pink to violet color, are soluble in most organic solvents and most are water insoluble.

Such rifamycin compounds are obtained by a method wherein a rifamycin compound having the formula

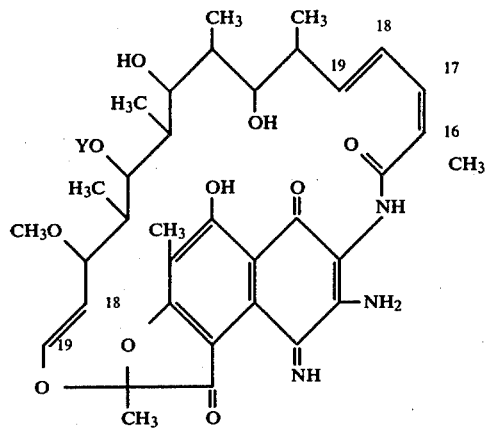

wherein Y is —H or —COCH₃; its 16, 17, 18, 19-tetrahydroderivatives and 16, 17, 18, 19, 28, 29-hexahydroderivatives, is reacted with a ketone having the formula

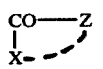

(III)

wherein X and Z are those as above defined, and X and Z along with CO form a ring selected from the group consisting of a hydrocarbon ring with less than 7 carbon atoms, a hydrocarbon ring with less than 7 carbon atoms substituted with at least one radical selected from the group comprising alkyl with less than 4 carbon atoms, halogen and carbalkoxy, as one having less than 4 carbon atoms, a heterocyclic ring with less than 7 atoms containing one N atom, such as the piperidine ring, a heterocyclic ring with less than 7 atoms containing one N atom, such as the piperidine ring, and substituted with a radical selected from the group consisting of linear alkyl having from 1 to 8 carbon atoms, branched alkyl having from 3 to 8 carbon atoms, alkenyl having 3 or 4 carbon atoms, cycloalkyl having from 3 to 6 carbon atoms, alkoxyalkyl having from 3 to 7 carbon atoms, arylalkyl with less than 9 carbon atoms, alkyl-furyl having 5 or 6 carbon atoms, alkyl tetrahydrofuryl having 5 or 6 carbon atoms, carbalkoxy, in particular carbalkoxy having less than 4 carbon atoms, alkanoyl having from 2 to 6 carbon atoms, and haloalkanoyl having from 2 to 6 carbon atoms and one haloatom only.

When formula III corresponds to the piperidine ring or the substituted piperidine ring, a suitable ketone is of the formula

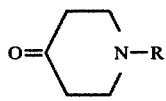

(IIIA)

where R is hydrogen or a substituent on the piperidine ring as defined following formula (I) and formula (IA).

The compound of formula (II) and methods of preparing the same are disclosed in applicants' patent application Ser. No. 680,771, filed Apr. 27, 1976, now U.S. Pat. No. 4,017,481, issued Apr. 12, 1977.

It has been found that the reaction of a ketone of formula (III) with the compound of formula (II) is more readily carried out and with improved yields when such a reaction is effected in the presence of acetic acid and a reducing agent selected from the group consisting of zinc and iron. Ammonium acetate together with zinc is also helpful in achieving improved results.

In order that the present invention be more clearly understood, some unrestrictive examples thereof will now be shown.

EXAMPLE 1

10 g 3-amino-4-deoxo-4-imino-rifamycin S were dissolved in 20 ml cyclohexanone. The solution was added with 1 g zinc, 20 ml acetic acid and stirred for 60 minutes at room temperature. Unreacted zinc was filtered, and the reaction solution was added with 100 ml dichloromethane, washed with water, dried on sodium sulphate and evaporated to dryness. The residue was dissolved again with 30 ml dichloromethane, the solution added with 200 ml petroleum ether, the precipitate obtained was filtered, then concentrating to 50 ml. 4.8 g were crystallized of a product of formula (I), wherein Y is —COCH₃ and X and Z, along with the C atom to which they are bonded, form a cyclohexylidene radical. The chemical-physical characteristics of the product are as follows:

the electronic absorption spectrum in methanol shows peaks at 495, 315 and 275 nm;

I.R. spectrum in nujol shows absorption bands in the region about 3250, and then at 1725, 1665, 1600, 1560, 1515, 1295, 1250, 1775–1155, 1060, 970, 920, 890, 765 and 725 cm⁻¹;

nuclear magnetic resonance spectrum in deuteratedchloroform, using tetrametylsilane as internal standard, shows the most significant peaks at θ: 0.60(d); 0.83(d); 1.05(d); 3.10(s); 4.81(dd); 5.15(dd); 8.23(s); 9.20(s) and 14.75(s) p.p;m. Also the disappearance of the last three said peaks, when in presence of deuterated water is characteristic.

EXAMPLE 2

10 g 3-amino-4-deoxo-4-imino-rifamycin S were dissolved in 25 ml methylisobutylketone. The solution was added with 1 g zinc, 30 ml acetic acid and heated at 40° C. for 30 minutes. Excess zinc was filtered, the reaction solution was added with 100 ml dichloromethane and washed with water. After drying on sodium sulphate and concentration to 20 ml, 100 ml cyclohexane and 50 petroleum ether were added. The solution was filtered and the filtered solution was evaporated to dryness.

Yield: 4.4 g product of formula (I), wherein Y is —COCH₃, X is methyl and Z is isobutyl, with the following chemical-physical characteristics:

the electronic absorption spectrum in methanol shows peaks at 500, 310 and 275 nm;

I.R. spectrum in nujol oil shows the most significant peaks at: 3400 (sh), 3250, 1725, 1620, 1600, 1560, 1510, 1415, 1290, 1250, 1155, 1060, 970, 945, 915, 890, 810 and 720 cm⁻¹.

EXAMPLE 3

8 g 3-amino-4-deoxo-4-imino-rifamycin S were mixed with 2.5 g iron and dissolved in 15 ml acetone and 15 ml acetic acid. After stirring at 35° C. for 15 minutes, excess iron was filtered and the solution poured into 600 ml water. The solution was filtered, washed with water, the aqueous phase extracted with toluene after correcting pH to 7 with bisodic phospahte. Toluene was concentrated to 20 ml and then diluted with 80 ml cyclohexane. After filtering, the mixture of the two solvents was evaporated, obtaining 3.5 g product of formula (I), wherein Y is —COCH$_3$, Z and X are methyl, and with the following chemical-physical characteristics:

the electronic absorption spectrum in methanol shows peaks at 490, 350(sh), 315 and 270 nm;

I.R. spectrum in nujol shows the most significant peaks at: 3400 (sh), 3250, 1730, 1675, 1650(sh), 1605, 1565, 1515, 1420, 1300, 1250, 1170, 1085, 1065, 975, 950, 930, 895, 815 and 690 cm$^{-1}$.

EXAMPLE 4

8 g 3-amino-4-deoxo-4-imino-rifamycin S were dissolved in 25 ml dioxane, added with 6 g 1-methyl-4-piperidone dissolved in 5 ml dioxane and heated at 70° C. for 10 minutes. The solution was poured into 400 ml water containing 20 g sodium chloride, the precipitate filtered, the filtrate extracted with chloroform, the organic phase dried on sodium sulphate and the solvent evaporated. The residue obtained was dissolved in benzene and the solution extracted with an aqueous solution of bisodic phosphate. Benzene was washed with water, the solution dried on sodium sulphate and then evaporated to dryness. Yield: 2.2 g product of formula (I), wherein Y is —COCH$_3$, and X and Z, along with the C atom to which they are bonded, form a 4-(1-methyl) piperidinylidene radical. The chemical-physical characteristics of the product are as follows:

The electronic absorption spectrum in methanol shows peaks at 485, 350(sh), 310 and 270 nm;

I.R. spectrum in nujol shows the most significant peaks at: 3400(sh), 3250, 1730, 1670, 1650(sh), 1605, 1565, 1515, 1420, 1300, 1255, 1180, 1160, 1065, 1015, 975, 950(sh), 920, 895, 815, 770 and 695 cm$^{-1}$;

nuclear magnetic resonance spectrum in deuterated chloroform, using tetramethylsilane as internal standard, shows the most significant peaks at $\theta$: —0.16(d); 0.60(d); 0.86(d); 1.04(d); 1.77(s); 2.02(s); 2.06(s); 2.32(s); 2.49(s); 3.10(s); 4.82(d); 5.14(dd); 5.70–6.60(m); 7.0–7.4(m); 8.27(s); 8.97(s) and 14.67(s) p.p.m. Also the disappearance of the last three said peaks, when in the presence of deuterated water, is characteristic.

EXAMPLE 5

8 g 3-amino-4-deoxo-4-imino-rifamycin S were reacted with 1 g zinc, 15 ml tetrahydrofuran, 8.5 ml 1-carbethoxy-4-piperidone and 25 ml acetic acid at 50° C. for 10 minutes. The reaction mixture was filtered and diluted with 200 ml xylene, washed with a phosphate buffer solution at pH 7.5, then with water and finally dried on sodium sulphate. Xylene was then evaporated to obtain 100 ml solution, which was diluted with 150 ml petroleum ether, filtered and evaporated to dryness. The residue obtained was added again with petroleum ether, filtered and dried. Yield: 5 g product of formula (I), wherein Y is —COCH$_3$ and X and Z, along with the C atom to which they are bonded, form a 4-(1-carbethoxy)-piperidinylidene radical.

The electronic absorption spectrum in methanol shows peaks at 500, 360(sh), 312 and 275 nm.

EXAMPLE 6

8 g 3-amino-4-deoxo-4-imino-rifamycin S were reacted with 1 g zinc, 10 ml tetrahydrofuran, 12 ml chloroacetone and 25 ml acetic acid. After 5 minutes at 60° C., the reaction was completed and after filtering unreacted zinc, the solution was poured into 800 ml buffered solution at pH 7.5 and containing 5 g ascorbic acid. The precipitate obtained was filtered, washed with water and vacuum dried at 40° C. Finally, the residue was continuously extracted with petroleum ether and by solvent evaporation 3.6 g product of formula (I) are obtained, wherein Y is —COCH$_3$, X is methyl and Z is chloromethyl.

The electronic absorption spectrum in methanol shows peaks at 495, 270, 238 and 210 nm.

EXAMPLE 7

8 g 3-amino-4-deoxo-4-imino-rifamycin S were reacted with 1 g zinc, 15 ml tetrahydrofuran, 8 ml 1-benzyl-4-piperidone and 30 ml acetic acid. After stirring at 60° C. for 15 minutes, unreacted zinc was filtered, then adding 1 g ascorbic acid, diluting with 300 ml xylene and washing with phosphate buffer solution at pH 7.5 and then with water. After drying the solution on sodium sulphate, the solvent was evaporated to dried residue, which was then continuously extracted with petroleum ether.

After solvent evaporation, 2.5 g product of formula (I) were then obtained, wherein Y is —COCH$_3$, and X and Z, along with the C atom to which they are bonded, form a 4-(1-benzyl)-piperidinylidene radical.

The electronic absorption spectrum in methanol shows peaks at 500, 315 and 275 nm.

EXAMPLE 8

8 g 3-amino-4-deoxo-4-imino-16, 17, 18, 19-tetrahydrorifamycin S were reacted with 1 g zinc, 15 ml tetrahydrofuran, 6 ml diethylaminoacetone and 30 ml acetic acid. After stirring at room temperature for 15 minutes, excess zinc was filtered, adding 1 g ascorbic acid and dropwise pouring the solution into 700 ml water.

The precipitate obtained was filtered and dissolved again in minimum volume of methyl alcohol. The methanol solution was diluted with 250 ml ethyl ether and then extracted with phosphate buffer solution at pH 7.5. The aqueous layer was acidified to pH 3 and then extracted with chloroform. The chloroform layer was washed with water, dried on sodium sulphate and evaporated to dryness. Thus, 0.8 g were obtained of 16, 17, 18, 19-tetrahydroderivative of a product of formula (I), wherein Y is —COCH$_3$, X is methyl and Z is diethylaminomethyl.

The electronic absorption spectrum in methanol shows peaks at 455 and 320 nm.

EXAMPLE 9

8 g 3-amino-4-deoxo-4-imino-16, 17, 18, 19, 28, 29-hexahydro-25-desacetyl-rifamycin S were reacted with 1 g zinc, 15 ml tetrahydrofuran, 4.5 g 1-acetyl-4-piperidone and 25 ml acetic acid. After stirring at room temperature for 30 minutes, unreacted zinc was filtered, adding 1 g ascorbic acid and diluting with 300 ml ethyl ether. The ether solution was thoroughly washed with water and then dried on sodium sulphate. Then, the residue was diluted with 50 ml petroleum ether, filtered and evaporated to dryness. 1.7 g 16, 17, 18, 19, 28, 29-hexahydroderivative of a product of formula (I) were obtained, wherein Y is —H and X and Z, along with the C atom to which they are bonded, form a 4-(1-acetyl)-piperidinylidene radical.

The electronic absorption spectrum in methanol shows peaks at 495, 315 and 275 nm.

EXAMPLE 10

8 g 3-amino-4-deoxo-4-imino-rifamycin S were reacted with 1 g zinc, 15 ml tetrahydrofuran, 2.5 g methylcyclopropylketone and 25 ml acetic acid. After 30 minutes at 50° C., unreacted zinc was filtered, the solution was diluted with 100 ml benzene and 300 ml ethyl ether and then washed with phosphate buffer solution at pH 7.5 and finally with water. The organic layer was evaporated, the residue reacted again with 30 ml methyl alcohol and after addition of 5 ml water containing 1 g sodium ascorbate, the solution was dropwise poured into 300 ml saturated aqueous solution of sodium metabisulphite. The precipitate obtained was filtered, washed with water and dried, 2.2 g product of formula (I) were obtained, wherein Y is —$COCH_3$, X is methyl and Z is cyclopropyl.

The electronic absorption spectrum in methanol shows peaks at 500 and 320 nm.

EXAMPLE 11

8 g 3-amino-4-deoxo-4-imino-rifamycin S dissolved in 25 ml tetrahydrofuran were dropwise added to a mixture comprising 1 g zinc, and 5 g 4-phenyl-butan-2-one preheated at 60° C. After stirring at 60° C. for 30 minutes, unreacted zinc was filtered, the mixture was added with 1 g ascorbic acid and diluted with 250 ml benzene. The mixture was then thoroughly washed with water, dried on sodium sulphate and benzene evaporated.

The residue obtained was dissolved in minum volume of methyl alcohol, the solution was treated with 5 ml water containing 1 g sodium ascorbate and then poured into 1000 ml water. The precipitate obtained was filtered, washed with water and dried. The product was dissolved again in 40 ml benzene, added with 80 ml petroleum ether, filtered and the solution was evaporated. The residue obtained of violet colour was added with water and filtrate. After drying, 2.8 g product of formula (I) were obtained, wherein Y is —$COCH_3$, X is methyl and Z is $\beta$-phenethyl. The electronic absorption spectrum in methanol shows peaks at 500 and 315 nm.

EXAMPLE 12

8 g 3-amino-4-deoxo-4-imino-rifamycin S were dissolved in 40 ml dichloromethane and reacted with 2.6 g 1-n-hexyl-4-piperidone at +5° C. for 48 hours. The solution was diluted with 600 ml ethyl ether, filtered and washed with water.

The organic phase was dried on sodium sulphate and then evaporated to dryness. The residue was extracted with ligroin and the violet solution evaporated to dryness.

Yield: 2.5 g product of formula (I), wherein Y is —$COCH_3$, and X and Z, along with the C atom to which they are bonded, form a 4-(1-n-hexyl)-piperidinylidene radical.

The electronic absorption spectrum in methanol shows peaks at 497, 314, 278 and 239 nm.

EXAMPLE 13

8 g 3-amino-4-deoxo-4-imino-rifamycin S were dissolved in 40 ml tetrahydrofuran. 4 g 1-(1',3'-dimethyl) butyl-4-piperidone, 0.5 g zinc and 0.5 g ammonium acetate were added and the mixture was stirred at room temperature for 30 minutes. The reaction mixture was worked up as in the example No. 12 obtaining 3.5 g of a product of formula (I), wherein Y is —$COCH_3$ and X and Z, along with the C atom to which they are bonded, form a 4-[1-(1',3'-dimethyl)-butyl]-piperidinylidene radical. The electronic absorption spectrum in methanol shows peaks at 500, 315, 277 and 240 nm.

EXAMPLE 14

8 g 3-amino-4-deoxo-4-imino-rifamycin S were dissolved in 40 ml tetrahydrofuran.1.8 gl-methallyl-4-piperidone, 0.2 g zinc and 0.2 g ammonium acetate were added and the mixture was allowed to stand at +5° C. for one night.

Reaction mixture was worked up as in the example No. 12 obtaining 5.5 g product of formula (I), wherein Y is —$COCH_3$, and X and Z, along with the C atom to which they are bonded, form a 4-(1-methallyl)-piperidinylidene radical.

The electronic absorption spectrum in methanol shows peacks at 498, 313, 275 and 238 nm.

EXAMPLE 15

8 g 3-amino-4-deoxo-4-imino-rifamycin S were dissolved in 40 ml tetrahydroduran. 3 g 1-cyclohexyl-4-piperidone, 0.2 g zinc and 0.2 ammonium acetate were added and the mixture was sittred 2.5 hours at room temperature. Unreacted zinc was filtered and the solution diluted with 1000 ml ethyl ether.

The ethereal solution was washed with buffer sodium phosphate solution at pH 7.8 and then extracted with diluted acetic acid. The violet aqueous solution was extracted with chloroform, the organic phase was washed and then dried on sodium sulfate. The chloroform was evaporated to dryness. Yield: 3.8 g product of formula (I), wherein Y is —$COCH_3$, and X and Z, along with the C atom to which they are bonded, form a 4-(1-cyclohexyl)-piperidinylidene radical.

The electronic absorption spectrum in methanol shows peaks at 498, 312, 273 and 235 nm.

EXAMPLE 16

8 g 3-amino-4-deoxo-4-imino-rifamycin S were dissolved in 40 ml tetrahydroduran. 0.5 g zinc, 0.5 g ammonium acetate and 5.5 g 1-(methylfuryl)-4-piperidone were added and the mixture was stirred at room temperature for 24 hours.

The reaction mixture was filtered, diluted with 500 ml diethyl ether and washed with water.

The organic phase was concentrated at 250 ml and then extracted with aqueous diluted acetic acid.

The violet, aqueous solution was extracted with dichloromethane and the organic phase, washed with water and dried on sodium sulfate was evaporated to dryness.

Yield: 3.3 g product of formula (I) wherein Y is —$COCH_3$ and X and Z, along with the C atom to which they are bonded, form a 4-(1-methylfuryl)-piperidinylidene radical.

The electronic absorption spectrum in methanol shows peaks at 497, 316, 276 and 240 nm.

EXAMPLE 17

8 g 3-amino-4-deoxo-4-imino-rifamycin S were dissolved in 40 ml tetrahydrofuran and dropped at 50° C. in a mixture of 15 ml tetrahydrofuran, 5 ml acetic acid, 1 g zinc and 5 g 1-(methyl-tetrahydrofuryl)-4-piperidone.

Heating is continued for 30 minutes and then the reaction mixture was worked up as in the example No. 16.

Yield: 2.1 g product of formula (I) wherein Y is —COCH₃ and X and Z, along with the C atom to which they are bonded, form a 4 (1-methyltetrahydrofuryl)-piperidinylidene radical.

The electronic absorption spectrum in methanol shows peaks at 495, 314, 275 and 239 nm.

EXAMPLE 18

32 g 3-amino-4-deoxo-4-imino-rifamycin S were dissolved in 200 ml tetrahydrofuran. 9 g 4-piperidone monohydrate hydrochloride, 10 g ammonium acetate and 0.4 g zinc were added and the mixture was stirred at room temperature for 12 hours.

The reaction mixture was filtered and dropped into 1500 ml diluted acetic acid. After filtration the aqueous solution was neutralized with sodium bicarbonate at pH 6 and then extracted twice with dichloromethane.

Yield: 13.4 g product of formula (I), wherein Y is —COCH₃ and X and Z, along with the C atom to which they are bonded, form a 4-piperidinylidene radical.

The electronic absorption spectrum in methanol shows peaks at 500, 315, 275 and 240 nm.

EXAMPLE 19

8 g 3-amino-4-deoxo-4-imino-rifamycin S were dissolved in 50 ml tetrahydrofuran. 0.3 g zinc, 0.3 g ammonium acetate and 2.5 g 1-chloroacetyl-4-piperidone were added and the mixture allowed to react at +5° C. for 48 hours.

The reaction mixture was filtered and diluted with 150 ml dichloromethane and 800 ml cyclohexane.

The solution was filtered again, washed with buffer sodium phosphate solution at pH 7.5 and then with water.

The solvent was evaporated under vacuum and the residue was crystallized from cyclohexane.

Yield: 3.2 g product of formula (I), wherein Y is —COCH₃, and X and Z, along with the C atom to which they are bonded, form a 4-(1-chloroacetyl)-piperidinylidene radical.

The electronic absorption spectrum in methanol shows peaks at 497, 310, 273 and 235 nm.

EXAMPLE 20

8 g 3-amino-4-deoxo-4-imino-rifamycin S were dissolved in 40 ml tetrahydrofuran. 0.5 g zinc, 5 ml acetic acid and 4.5 g 1-n-octyl-4-piperidone were added and the mixture was stirred ten minutes at room temperature.

Unreacted zinc was filtered and the solution diluted with 700 ml diisopropyl-ether. The solution was filtered again and concentrated to 300 ml under vacuum.

300 ml petroleum ether were added and the solution was filtered once more. After evaporation of the solvent the oily residue was dissolved in 40 ml methanol and the solution was dropped in 400 ml water.

The obtained precipitate was filtered, washed with water and dried at 40° C. under vacuum.

Yield: 3.8 g product of formula (I), wherein Y is —COCH₃, and X and Z, along with the C atom to which they are bonded, form a 4-(1-n-octyl)-piperidinylidene radical.

The electronic absorption spectrum in methanol shows peaks at 497, 310, 274 and 236 nm.

EXAMPLE 21

16 g 3-amino-4-deoxo-4-imino-rifamycin S were dissolved in 100 ml tetrahydrofuran. 1 g zinc, 0.5 g ammonium acetate and 8 g 1-(3'-methoxy) propyl-4-piperidone were added and the mixture was stirred at room temperature for 60'.

The reaction mixture was filtered, diluted with 1500 ml xylene and washed with water. The organic phase was extracted with diluted acetic acid and then discharged.

The aqueous solution, buffered at pH 7 with sodium phosphate solution, was extracted with dichloromethane.

After dilution with petroleum ether the violet solution was filtered and then evaporated to dryness. Yield: 3.0 g product of formula (I), wherein Y is —COCH₃, and X and Z, along with the C atom to which they are bonded, form a 4[1-(3'-methoxy-propyl)] piperidinylidene radical.

Thin layer chromatography on silica gel plates, using chloroform-methanol 9:1 as mobile phase, showed one violet spot with Rf=0.48.

EXAMPLE 22

8 g 3-amino-4-deoxo-4-imino-rifamycin S were dissolved in 40 ml tetrahydrofuran. 0.5 g zinc, 0.5 g ammonium acetate and 4.5 g 1-(1',4'-dimethyl) pentyl-4-piperidone were added and the mixture was stirred at room temperature for 30'.

The reaction mixture was worked up as in the example No. 21.

Yield: 5.0 g product of formula (I) wherein Y is —COCH₃ and X and Z, along with the C atom to which they are bonded, form a 4-[1-(1',4'-dimethyl-pentyl)-]piperidinylidene radical.

Thin layer chromatography on silica gel plates, using chloroform-methanol 9:1 as mobile phase, showed one violet spot with Rf=0.52.

EXAMPLE 23

8 g 3-amino-4-deoxo-4-imino-rifamycin S were dissolved in 50 ml tetrahydrofuran. 0.2 g zinc, 0.2 g ammonium acetate and 3 g 1-pivaloyl-4-piperidone were added and the mixture was kept at 0° C. for 3 days. The reaction mixture was filtered, diluted with 300 ml diethyl ether and washed with buffer sodium phosphate solution at pH 7.5. The organic phase was washed with water, dried on sodium sulfate and evaporated to dryness.

The residue was crystallized from cyclohexane.

Yield: 7 g product of formula I wherein Y is —COCH₃ and X and Z, along with the C atom to which they are bonded, form a 4-(1-pivaloyl)-piperidinylidene radical.

The electronic absorption spectrum in methanol shows peaks at 497, 316, 276 and 238 nm.

What we claim is:

1. A rifamycin compound having the formula

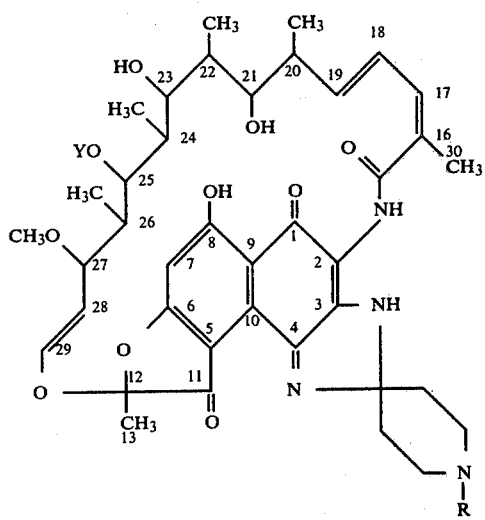

wherein R is a radical selected from the group consisting of linear alkyl having 4 to 8 carbon atoms, branched alkyl having 4 to 8 carbon atoms, and Y is —H or —COCH₃, and the 16, 17, 18, 19-tetrahydro derivatives and the 16, 17, 18, 19, 28, 29-hexahydro derivatives thereof.

2. The compound of claim 1, wherein the radical R is selected from the group consisting of linear and branched alkyls having 4 or 5 carbon atoms.

3. The compound of claim 1 wherein the radical R is linear alkyl having 4 to 8 carbon atoms.

4. The compound of claim 1 wherein the radical R is branched alkyl having 4 to 8 carbon atoms.

5. A method of preparing a rifamycin compound of claim 3, which comprises reacting a compound having the formula

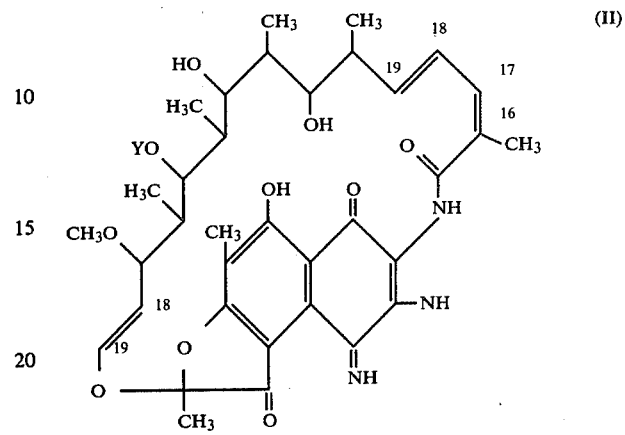

wherein Y is —H or —COCH₃, its 16, 17, 18, 19-tetrahydroderivatives or its 16, 17, 18, 19, 28, 29-hexahydroderivatives, with a ketone having the formula

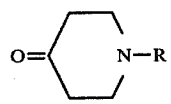

where R is defined in claim 3.

* * * * *

UNITED STATES PATENT AND TRADEMARK OFFICE
CERTIFICATE OF CORRECTION

PATENT NO. : 4,219,478                    Page 1 of 2
DATED     : June 26, 1980
INVENTOR(S) : LEONARDO MARSILI ET AL It is certified that error appears in the above—identified patent and that said Letters Patent is hereby corrected as shown below:

The structural formula at column 11, lines 1-22 should read as follows --

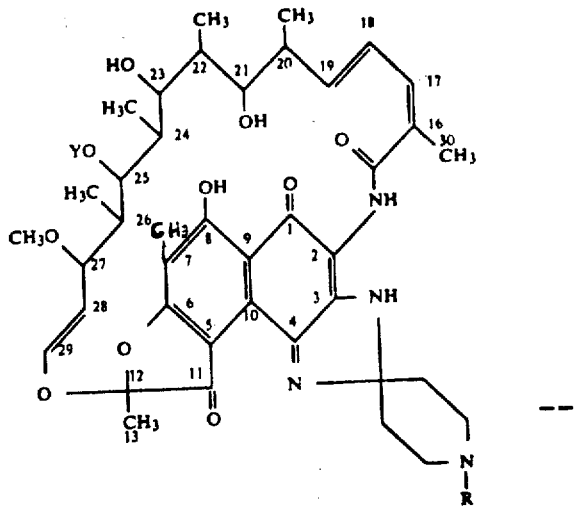

The structural formula at column 12, lines 6-22 should read as follows

UNITED STATES PATENT AND TRADEMARK OFFICE
CERTIFICATE OF CORRECTION

PATENT NO. : 4,219,478

DATED : June 26, 1980

INVENTOR(S) : RIFAMYCIN COMPOUNDS

It is certified that error appears in the above—identified patent and that said Letters Patent is hereby corrected as shown below:

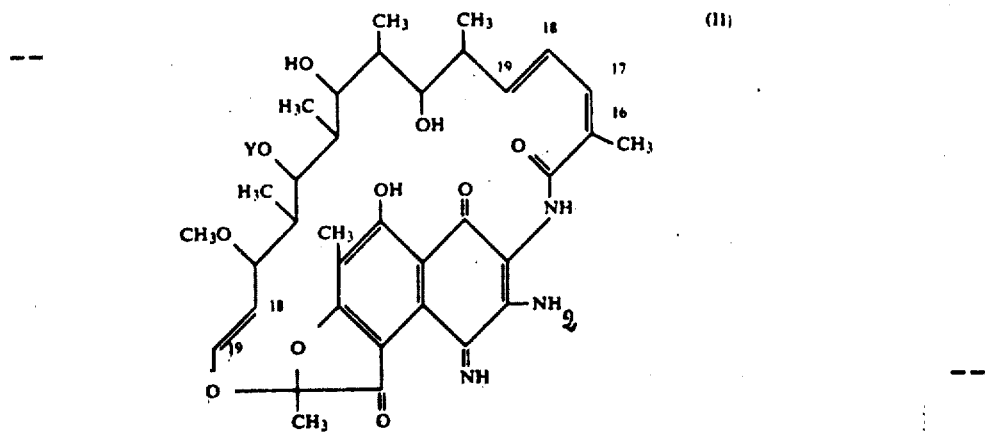

Signed and Sealed this

Fourteenth Day of April 1981

[SEAL]

Attest:

RENE D. TEGTMEYER

Attesting Officer

Acting Commissioner of Patents and Trademarks

UNITED STATES PATENT AND TRADEMARK OFFICE

CERTIFICATE EXTENDING PATENT TERM
UNDER 35 U.S.C. § 156

PATENT NO.      : 4,219,478

DATED           : August 26, 1980

INVENTOR(S)     : Leonardo Marsili et al.

PATENT OWNER    : Farmitalia Carlo Erba S.r.l.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,406 DAYS with all rights pertaining thereto as provided by 35 U.S.C. § 156(b).

I have caused the seal of the Patent and Trademark Office to be affixed this 23rd day of January 1996.

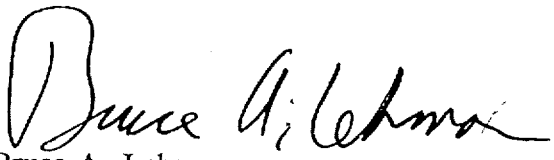

Bruce A. Lehman
Assistant Secretary of Commerce and
Commissioner of Patents and Trademarks